(12) United States Patent
Hanabusa et al.

(10) Patent No.: US 9,198,846 B2
(45) Date of Patent: Dec. 1, 2015

(54) BASIC AMINO ACID DERIVATIVE

(71) Applicant: AJINOMOTO CO., INC., Tokyo (JP)

(72) Inventors: Kenji Hanabusa, Ueda (JP); Masahiro Suzuki, Ueda (JP); Takanori Sugimoto, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/452,892

(22) Filed: Aug. 6, 2014

(65) Prior Publication Data

US 2014/0350128 A1 Nov. 27, 2014

Related U.S. Application Data

(63) Continuation of application No. PCT/JP2013/053148, filed on Feb. 8, 2013.

(30) Foreign Application Priority Data

Feb. 9, 2012 (JP) .................. 2012-025684

(51) Int. Cl.
| | |
|---|---|
| *C07C 235/74* | (2006.01) |
| *A61K 8/04* | (2006.01) |
| *A61K 8/44* | (2006.01) |
| *A61Q 5/00* | (2006.01) |
| *A61Q 5/12* | (2006.01) |
| *A61Q 17/04* | (2006.01) |
| *A61Q 19/00* | (2006.01) |
| *A61Q 19/10* | (2006.01) |
| *C07C 233/47* | (2006.01) |

(52) U.S. Cl.
CPC . *A61K 8/44* (2013.01); *A61K 8/042* (2013.01); *A61K 8/442* (2013.01); *A61Q 5/00* (2013.01); *A61Q 19/00* (2013.01); *A61Q 19/10* (2013.01); *C07C 233/47* (2013.01); *C07C 235/74* (2013.01); *A61K 2800/10* (2013.01); *A61Q 5/12* (2013.01); *A61Q 17/04* (2013.01)

(58) Field of Classification Search
None
See application file for complete search history.

(56) References Cited

U.S. PATENT DOCUMENTS

| 6,921,747 B2 * | 7/2005 | Hanabusa et al. ............ 514/18.8 |
| 2004/0248812 A1 | 12/2004 | Hanabusa et al. |
| 2010/0215603 A1 | 8/2010 | Kanda et al. |

FOREIGN PATENT DOCUMENTS

| JP | 2004-323505 A | 11/2004 |
| WO | WO 2006/134890 A1 | 12/2006 |

OTHER PUBLICATIONS

Ghaffar et al., Biomacromolecules, 2011, 12, pp. 3243-3251.*
STN Registry database entry for CAS RN 1175792-55-8 (Published in STN Registry Nov. 16, 1990); Accessed Aug. 18, 2015.*
U.S. Appl. No. 14/453,036, filed Aug. 6, 2014, Hanabusa, et al.
International Search Report issued Apr. 23, 2013 in PCT/JP2013/053148.
Shin-ichi Nagao, et al., "Augmentation by Priming with Interferon-y of the Binding of a Muramyl Dipeptide Derivative to Macrophages Resulting in Synergistic Macrophage Activation," Jpn. J. Cancer Res. (Gann), 78, Jan. 1987, pp. 80-86.
Takanori Kasai, et al., "γ-Glutamyl Peptides of Vigna Radiata Seeds," Phytochemistry, vol. 25, No. 3, 1986, pp. 679-682.
Kozo Okada, et al., "Mass Spectral Differentiation of a- and γ-Linkages in Glutamyl Oligopeptides and Its Application for Structure Elucidation of Naturally Occuring Peptides," Chem. Pharm. Bull. vol. 25, No. 7, 1977, pp. 1497-1508.
Koji Daigo, et al., "Synthesis of Some N-Lipoyl Amino Acids and Peptides," Journal of the American Chemical Society, vol. 84,1962, pp. 662-665.
Lili Lou, et al., "Biosynthesis of HSAF, a Tetramic Acid-Containing Macrolactam from Lysobacter Enzymogenes," JACS., 2011, pp. 643-645.
A. Laghmich, et al., "New Esters of Succinic Acid and Mixed Molecules Formed by such Esters and a Meglitinide Analog: Study of their Insulinotropic Potential," Pharmacological Research, vol. 41, No. 5, 2000, pp. 543-554.
Masahiro Suzuki, et al., "Low-molecular-weight Gelators Based on $N^{\alpha}$-acetyl-$N^{\epsilon}$-dodecyl-L-lysine and their Amphiphilic Gelation Properties," Journal of Colloid and Interface Science, 341, 2010, pp. 69-74.
M. Suzuki, et al., "Supramolecular Gels Formed by Amphiphilic Low-Molecular-Weight Gelators of $N^{\alpha},N^{\epsilon}$-Diacyl-L-Lysine Derivatives," Chem. Eur. J. 2008, pp. 2133-2144.

* cited by examiner

*Primary Examiner* — Alicia L Otton
(74) *Attorney, Agent, or Firm* — Oblon, McClelland, Maier & Neustadt, L.L.P.

(57) ABSTRACT

Provided is a compound capable of gelling various aqueous compositions containing salt, acid and the like.
A basic amino acid derivative represented by the formula (1):

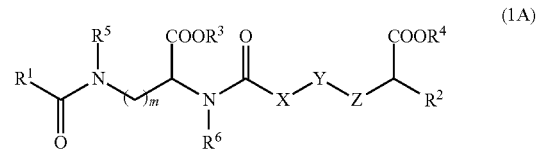

(1A)

wherein each substituent is as defined in DESCRIPTION, or a salt thereof.

6 Claims, No Drawings

BASIC AMINO ACID DERIVATIVE

CROSS REFERENCES TO RELATED APPLICATIONS

This application is a continuation of International Patent Application No. PCT/JP2013/053148, filed on Feb. 8, 2013, and claims priority to Japanese Patent Application No. 2012-025684, filed on Feb. 9, 2012, both of which are incorporated herein by reference in their entireties.

BACKGROUND OF THE INVENTION

1. Field of the Invention

The present invention relates to a basic amino acid derivative that demonstrates a gelling ability in a water system.

2. Discussion of the Background

A method of controlling fluidity of compositions that are liquid at ambient temperature such as cosmetic agents, pharmaceuticals, agricultural chemicals, feeds, fertilizers, paints and the like, and processing them into a form fitted for diversified use objects is an industrially very important technique. When the fluidity of an aqueous composition is controlled, water-soluble polymers such as carboxyvinyl polymer, xanthan gum and the like are generally used. In a system containing a salt, however, gelling is difficult and a large amount of water-soluble polymer needs to be added. Use of a large amount of water-soluble polymer is associated with a problem of a degraded sense of use, since the effect of a functional component contained in an aqueous composition is not sufficiently demonstrated, stickiness increases in the case of cosmetic agents, and the like.

Patent document 1, and non-patent documents 1 and 2 describe amino acid derivatives as gelling agents. It is described that addition of a comparatively small amount of these gelling agents causes gelling of an aqueous solution containing a salt. However, the obtained gel composition is not entirely satisfactory in terms of smoothness, spinnability and the like.

DOCUMENT LIST

Patent Document patent document 1: JP-A-2004-323505

Non-Patent Documents non-patent document 1: Journal of Colloid and Interface Science 341(2010) 69-74
non-patent document 2: Chem. Eur. J. 2008, 14, 2133

SUMMARY OF THE INVENTION

Problems to be Solved by the Invention

The problem of the present invention is to provide a compound having a superior gelling ability, which can gel various aqueous compositions containing a salt or an acid by adding a small amount thereof. Furthermore, the problem is to provide a gel composition which is smooth and shows good spinnability.

Means of Solving the Problems

The present inventors have conducted intensive studies, and found that a particular basic amino acid derivative gels various aqueous compositions containing a salt or an acid, and further that a gel composition obtained by using this particular basic amino acid derivative is smooth and shows good spinnability, which resulted in the completion of the present invention:

Accordingly, the present invention is as follows.

[1] A basic amino acid derivative represented by the formula (1A):

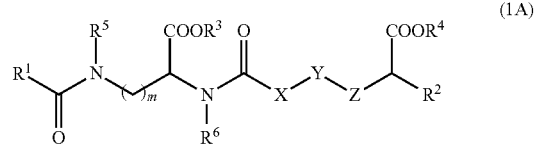

(1A)

wherein
an acyl group represented by $R^1$—CO— is an acyl group derived from an optionally substituted saturated or unsaturated fatty acid;
$R^2$ is a hydrogen atom or an optionally substituted hydrocarbon group;
m is an integer of 1-4;
$R^3$, $R^4$, $R^5$ and $R^6$ are each independently a hydrogen atom or an optionally substituted saturated or unsaturated straight chain or branched chain hydrocarbon group having 1-6 carbon atoms; and
X, Y and Z are each independently a single bond, or an optionally substituted divalent, hydrocarbon group, wherein 1-10 carbon atoms in the carbon atoms constituting the divalent hydrocarbon group are optionally substituted by hetero atom(s), and 1-10 carbon atoms in the carbon atoms constituting the divalent hydrocarbon group optionally have oxo group(s), or a salt thereof (hereinafter also referred to as the basic amino acid derivative of the present invention).

[2] The basic amino acid derivative of the above-mentioned [1], wherein the acyl group represented by $R^1$—CO— is an acyl group derived from optionally substituted saturated or unsaturated fatty acid having 2-18 carbon atoms,
$R^2$ is a hydrogen atom or an optionally substituted saturated or unsaturated straight chain or branched chain hydrocarbon group having 1-30 carbon atoms, and
X, Y and Z are each independently a single bond, or an optionally substituted divalent hydrocarbon group having 1-15 carbon atoms, wherein 1-10 carbon atoms in the carbon atoms constituting the hydrocarbon group are optionally substituted by hetero atom(s), and 1-10 carbon atoms in the carbon atoms constituting the hydrocarbon group optionally have oxo group(s), or a salt thereof.

[3] The basic amino acid derivative of the above-mentioned [1], which is represented by the formula (1B):

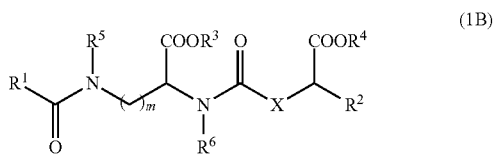

(1B)

wherein
an acyl group represented by $R^1$—CO— is an acyl group derived from an optionally substituted saturated or unsaturated fatty acid having 2-18 carbon atoms;

$R^2$ is a hydrogen atom or an optionally substituted saturated or unsaturated straight chain or branched chain hydrocarbon group having 1-30 carbon atoms;
m is an integer of 1-4;
$R^3$, $R^4$, $R^5$ and $R^6$ are each independently a hydrogen atom or an optionally substituted saturated or unsaturated straight chain or branched chain hydrocarbon group having 1-6 carbon atoms; and
X is a single bond, or an optionally substituted straight chain or branched chain divalent hydrocarbon group having 1-15 carbon atoms, wherein 1-10 carbon atoms in the carbon atoms constituting the hydrocarbon group are optionally substituted by hetero atom(s), and 1-10 carbon atoms in the carbon atoms constituting the hydrocarbon group optionally have oxo group(s), or a salt thereof.
[4] The basic amino acid derivative of the above-mentioned [1], which is represented by the formula (1):

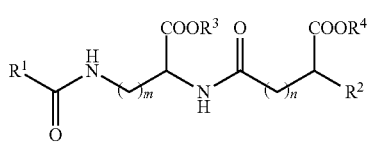

wherein
an acyl group represented by $R^1$—CO— is an acyl group derived from an optionally substituted saturated or unsaturated fatty acid having 2-18 carbon atoms;
$R^2$ is a hydrogen atom or an optionally substituted saturated or unsaturated straight chain or branched chain hydrocarbon group having 1-30 carbon atoms;
m is an integer of 1-4;
n is an integer of 0-15; and
$R^3$ and $R^4$ are each independently a hydrogen atom, or an optionally substituted saturated or unsaturated straight chain or branched chain hydrocarbon group having 1-6 carbon atoms, or a salt thereof.
[5] The basic amino acid derivative of the above-mentioned [4], wherein the acyl group represented by $R^1$—CO— is an acyl group derived from a saturated or unsaturated fatty acid having 6-18 carbon atoms,
$R^2$ is a hydrogen atom or a saturated or unsaturated straight chain or branched chain hydrocarbon group having 1-15 carbon atoms,
n is an integer of 0-9, and
$R^3$ and $R^4$ are each independently a hydrogen atom, or a saturated or unsaturated straight chain or branched chain hydrocarbon group having 1-6 carbon atoms, or a salt thereof.
[6] The basic amino acid derivative of any of [1]-[5], wherein $R^1$—CO— is a lauroyl group, and m is 4, or a salt thereof.
[7] The basic amino acid derivative of the above-mentioned [1], which is selected from the group consisting of $N^\epsilon$-lauroyl-$N^\alpha$-(3-carboxytridecanoyl)-L-lysine ethyl ester, $N^\epsilon$-lauroyl-$N^\alpha$-(3-carboxytridecanoyl)-L-lysine, $N^\epsilon$-lauroyl-$N^\alpha$-(5-carboxypentanoyl)-L-lysine, $N^\epsilon$-lauroyl-$N^\alpha$-(7-carboxyheptanoyl)-L-lysine, and $N^\epsilon$-lauroyl-$N^\alpha$-(9-carboxynonanoyl)-L-lysine, or a salt thereof.
[7'] The basic amino acid derivative of the above-mentioned [1], which is selected from the group consisting of $N^\epsilon$-lauroyl-$N^\alpha$-(3-carboxytridecanoyl)-L-lysine ethyl ester, $N^\epsilon$-lauroyl-$N^\alpha$-(3-carboxytridecanoyl)-L-lysine, $N^\epsilon$-lauroyl-$N^\alpha$-(5-carboxypentanoyl)-L-lysine, $N^\epsilon$-lauroyl-$N^\alpha$-(7-carboxyheptanoyl)-L-lysine monosodium salt, and $N^\epsilon$-lauroyl-$N^\alpha$-(9-carboxynonanoyl)-L-lysine, or a salt thereof.
[8] The basic amino acid derivative of the above-mentioned [1], which is $N^\epsilon$-lauroyl-$N^\alpha$-(9-carboxynonanoyl)-L-lysine or a salt thereof, or a salt thereof.
[9] A gelling agent comprising at least one kind of the basic amino acid derivatives of any of the above-mentioned [1]-[8] or a salt thereof.
[10] A gel composition comprising at least one kind of the basic amino acid derivatives of any of the above-mentioned [1]-[8] or a salt thereof, and water.
[11] A cosmetic agent comprising the gel composition of the above-mentioned [10].

Effect of the Invention

Using the basic amino acid derivative of the present invention, various aqueous compositions can be gelled, and further, a gel composition which is smooth and shows good spinnability can be provided. The gel composition controls fluidity of compositions that are liquid at ambient temperature such as cosmetic agents, pharmaceuticals, agricultural chemicals, feeds, fertilizers, paints and the like, and is useful for processing them into a form fitted for diversified use objects. Particularly, it is useful for cosmetic agents.

DETAILED DESCRIPTION OF THE PREFERRED EMBODIMENTS

In the present specification, "demonstrates more superior gelling ability" refers to an ability to gel by the addition of a smaller amount thereof.

In the present specification, the "saturated or unsaturated fatty acid" means, unless otherwise specified, "saturated fatty acid" or "unsaturated fatty acid", and also encompasses "fatty acid derived from natural fats and oils".

In the present specification, examples of the "saturated fatty acid" include saturated straight chain fatty acids such as acetic acid, propionic acid, butyric acid, valeric acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid, docosanoic acid and the like; saturated branched chain fatty acids such as isobutanoic acid, isopentanoic acid, neopentanoic acid, isohexanoic acid, isoheptanoic acid, 2-ethylhexanoic acid, isononanoic acid, isodecanoic acid, dimethyloctanoic acid, isoundecanoic acid, isododecanoic acid, 2-butyloctanoic acid, isotridecanoic acid, isotetradecanoic acid, isopentadecanoic acid, isohexadecanoic acid, 2-hexyldecanoic acid, isoheptadecanoic acid, isostearic acid, isononadecanoic acid, isoicosanoic acid, 2-octyldodecanoic acid, anteiso-heneicosanoic acid and the like; and cyclic fatty acids such as cyclohexanecarboxylic acid and the like.

In the present specification, examples of the "unsaturated fatty acid" include straight chain or branched chain unsaturated fatty acids such as undecenoic acid, myristoleic acid, palmitoleic acid, oleic acid, isooleic acid, linoleic acid, linolenic acid, elaidic acid, gadoleic acid, eicosapentaenoic acid, docosahexaenoic acid, erucic acid, brassidic acid, arachidonic acid and the like; and cyclic unsaturated fatty acids such as benzoic acid, nicotinic acid and the like.

In the present specification, examples of the "fatty acid derived from natural fats and oils" include coconut oil fatty acid, castor oil fatty acid, olive oil fatty acid, palm oil fatty acid and the like.

In the present specification, the "acyl group derived from fatty acid" means, unless otherwise specified, a substituent obtained by removing a hydroxyl group from a carboxy group of the above-mentioned "saturated fatty acid", "unsaturated fatty acid", "fatty acid derived from natural fats and oils" and the like.

In the present specification, examples of the "hydrocarbon group" include (i) chain hydrocarbon groups such as an alkyl group (methyl group, ethyl group, propyl group, isopropyl group, butyl group, isobutyl group, sec-butyl group, tert-butyl group, pentyl group, isopentyl group, sec-pentyl group, tert-pentyl group, hexyl group, heptyl group, octyl group and the like), an alkenyl group (vinyl group, 1-propen-1-yl group, 2-propen-1-yl group, isopropenyl group, 2-buten-1-yl group, 4-penten-1-yl group, 5-hexen-1-yl group and the like), an alkynyl group (ethynyl group, 1-propyn-1-yl group, 2-propyn-1-yl group, 4-pentyn-1-yl group, 5-hexyn-1-yl group and the like) and the like; (ii) alicyclic hydrocarbon groups such as a cycloalkyl group (cyclopropyl group, cyclobutyl group, cyclopentyl group and the like); a cycloalkenyl group (cyclopropenyl group, cyclobutenyl group, cyclopentenyl group and the like) and the like; and (iii) aromatic hydrocarbon groups such as an aryl group (phenyl group, naphthyl group and the like) and the like.

In the present specification, examples of the "divalent hydrocarbon group" include (i) divalent chain hydrocarbon groups such as an alkylene group [—(CH$_2$)$_{n'}$— (n' is an integer of 1-15), 1-methylethylene group, trimethylene group, 2-methyltrimethylene group, tetramethylene group and the like], an alkenylene group (vinylene, 2-butene-1,4-diyl, 1,2-dimethyl-1,2-ethenediyl and the like), an alkynylene group (ethynylene group, 2-butyne-1,4-diyl group and the like) and the like; (ii) divalent alicyclic hydrocarbon groups such as a cycloalkylene group [cyclopropylene, cyclobutylene (1,2-cyclobutylene, 1,3-cyclobutylene etc.), cyclopentylene (1,2-cyclopentylene, 1,3-cyclopentylene etc.), cyclohexylene (1,2-cyclohexylene, 1,3-cyclohexylene, 1,4-cyclohexylene etc.) and the like], a cycloalkenylene group [cyclopropenylene, cyclobutenylene, cyclopentenylene (1,3-cyclopent-1-enylene etc.), cyclohexenylene (1,3-cyclohex-1-enylene etc.) and the like] and the like; and (iii) divalent aromatic hydrocarbon groups such as an arylene group [phenylene(1,4-phenylene etc.), naphthalene-diyl(1,4-naphthalene-diyl, 2,6-naphthalene-diyl etc.), anthracene-diyl(9,10-anthracene-diyl, 1,4-anthracene-diyl etc.) and the like] and the like.

In the present specification, the "heterocyclic group" shows, unless otherwise specified, a 5- to 14-membered monocyclic-tricyclic heterocyclic group containing, besides carbon atom, 1-4 hetero atoms selected from an oxygen atom, a sulfur atom and a nitrogen atom. Therein, any carbon atom as a ring atom may be substituted by an oxo group, and the sulfur atom or nitrogen atom may be oxidized to form an oxide. The heterocyclic group may be fused with a benzene ring, or crosslinked, or may form a spiro ring.

In the present specification, examples of the "heterocycle" include rings corresponding to the above-mentioned "heterocyclic group".

Examples of the "halogen atom" in the present specification include a fluorine atom, a chlorine atom, a bromine atom, and an iodine atom.

In the present specification, examples of the substituent of the chain acyl group and chain hydrocarbon group from among the acyl group and hydrocarbon group include substituents selected from the following substituent group A. Examples of the substituent of the cyclic acyl group and cyclic hydrocarbon group from among the acyl group and hydrocarbon group, and the substituent of the nitrogen-containing heterocycle include substituent selected from the following substituent group A and substituent group B. The number of the substituents is 1-substitutable maximum number, more preferably 1-3, further preferably 1.

In the present specification, substituent group A comprises
(a) a halogen atom;
(b) a hydroxy group;
(c) a nitro group;
(d) a cyano group;
(e) a $C_{3-7}$ cycloalkyl group;
(f) a $C_{6-14}$ aryl group;
(g) a $C_{7-16}$ aralkyl group;
(h) a heterocyclic group;
(i) a $C_{1-6}$ alkoxy group;
(j) a $C_{3-7}$ cycloalkyloxy group;
(k) a $C_{6-14}$ aryloxy group;
(l) a $C_{7-16}$ aralkyloxy group;
(n) a heterocyclyl-oxy group;
(n) an amino group optionally mono- or di-substituted by substituent(s) selected from the group consisting of a $C_{1-6}$ alkyl group, a $C_{2-6}$ alkenyl group, a $C_{6-14}$ aryl group, a $C_{7-16}$ aralkyl group, and a heterocyclic group;
(o) a $C_{1-6}$ alkyl-carbonyl group;
(p) a $C_{3-7}$ cycloalkyl-carbonyl group;
(q) a $C_{6-14}$ aryl-carbonyl group;
(r) a $C_{7-16}$ aralkyl-carbonyl group;
(s) a heterocyclyl-carbonyl group;
(t) a mono- or di-$C_{1-6}$ alkyl-carbamoyl group;
(u) a mono- or di-$C_{6-14}$ aryl-carbamoyl group; and
(v) a mono- or di-heterocyclyl-carbamoyl group.

In the present specification, substituent group B comprises
(a) a $C_{1-10}$ alkyl group;
(b) a $C_{2-10}$ alkenyl group; and
(c) a $C_{2-10}$ alkynyl group.

In the present specification, the substituent shown by

in each formula is also indicated as "$R^1$—CO-".

The basic amino acid derivative of the present invention is represented by the formula (1A).

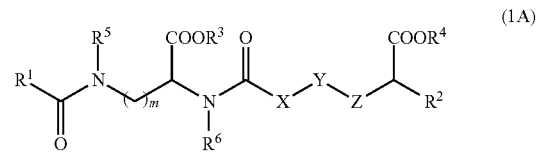

(1A)

The basic amino acid derivative of the present invention is preferably represented by the formula (1B).

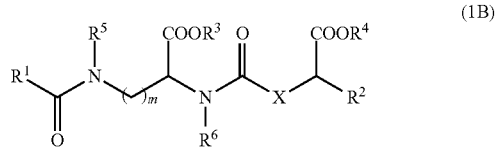

(1B)

The basic amino acid derivative of the present invention is more preferably represented by the formula (1).

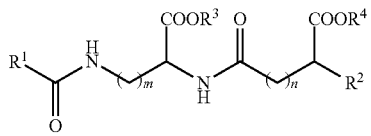

The definition of each symbol in the compounds represented by the formula (1A), the formula (1B) and the formula (1) is explained in detail below.

The acyl group represented by $R^1$—CO— is an acyl group derived from an optionally substituted saturated or unsaturated fatty acid. Examples thereof include an acyl group derived from an optionally substituted saturated fatty acid, an acyl group derived from an optionally substituted unsaturated fatty acid, an acyl group derived from fatty acid derived from an optionally substituted natural fats and oils and the like.

The acyl group represented by $R^1$—CO— is preferably an acyl group derived from a saturated or unsaturated fatty acid, more preferably an acyl group derived from a straight chain or branched chain saturated or unsaturated fatty acid.

In another embodiment, the acyl group represented by $R^1$—CO— is preferably an acyl group derived from an optionally substituted saturated or unsaturated fatty acid having 2-18 carbon atoms, more preferably an acyl group derived from a straight chain or branched chain saturated or unsaturated fatty acid having 2-18 carbon atoms. Examples thereof include an acetyl group, a propionyl group, a butyryl group, a valeryl group, a pivaloyl group, a hexanoyl group, a heptanoyl group, an octanoyl group, a 2-ethylhexanoyl group, a nonanoyl group, a decanoyl group, a lauroyl group, a myristoyl group, a palmitoyl group, a stearoyl group, an oleoyl group and a linoleyl group. The acyl group represented by $R^1$—CO— may be, besides an acyl group derived from fatty acid of a single composition, an acyl group derived from naturally-occurring mixed fatty acid or fatty acid obtained by synthesis (including branched fatty acid) such as coconut oil fatty acid, castor oil fatty acid, olive oil fatty acid, palm oil fatty acid and the like. One kind of these may be used, or two or more kinds selected from the above-mentioned groups may be used in a mixture. To demonstrate a more superior gelling ability, the acyl group represented by $R^1$—CO— is preferably an acyl group derived from saturated fatty acid having carbon number 6-18, more preferably derived from straight chain or branched chain saturated fatty acid having 6-18 carbon atoms, further preferably one kind selected from a lauroyl group, a myristoyl group, a palmitoyl group and a stearoyl group, particularly preferably a lauroyl group.

$R^2$ is a hydrogen atom or an optionally substituted hydrocarbon group, preferably a hydrogen atom or an optionally substituted saturated or unsaturated straight chain or branched chain hydrocarbon group, more preferably a hydrogen atom or an optionally substituted saturated or unsaturated straight chain or branched chain hydrocarbon group having 1-30 carbon atoms. Examples of the saturated or unsaturated straight chain or branched chain hydrocarbon group having 1-30 carbon atoms include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group, a heptyl group, an octyl group, a 2-ethylhexyl group, a tert-octyl group, a nonyl group, an isononyl group, a decyl group, an isodecyl group, an undecyl group, a dodecyl group, a tridecyl group, an isotridecyl group, a tetradecyl group, a pentadecyl group and the like.

In another embodiment, $R^2$ is preferably a hydrogen atom or a saturated or unsaturated straight chain or branched chain hydrocarbon group having 1-15 carbon atoms, more preferably a hydrogen atom or a saturated or unsaturated straight chain or branched chain hydrocarbon group having 4-15 carbon atoms, further preferably a hydrogen atom or a saturated or unsaturated straight chain or branched chain hydrocarbon group having 4-10 carbon atoms, particularly preferably a hydrogen atom or a saturated straight chain or branched chain hydrocarbon group having 7-10 carbon atoms.

m is an integer of 1-4. When m=3, an ornithine derivative is provided, and when m=4, a lysine derivative is provided. From the aspects of gelling ability and easy preparation, m is preferably 3 or 4, particularly preferably 4 (lysine derivative).

In the formula (1), n is an integer of 0-15, preferably an integer of 0-9.

The total number of carbon atoms of $R^2$ and $(CH_2)n$ is desirably an appropriate number of carbon atoms, from the aspects of gelling ability and solubility. The total number of carbon atoms of $R^2$ and $(CH_2)n$ is preferably 3-12, more preferably 3-11, further preferably 5-11, still more preferably 7-11. For example, when n=1, $R^2$ is preferably a saturated or unsaturated straight chain or branched chain hydrocarbon group having 2-11 carbon atoms, more preferably a hexyl group, a heptyl group, an octyl group, or a decyl group, further preferably a heptyl group or a decyl group. When $R^2$ is a hydrogen atom, n is preferably 3-12, more preferably 3-7.

$R^3$, $R^4$, $R^5$ and $R^6$ are each independently a hydrogen atom or an optionally substituted saturated or unsaturated straight chain or branched chain hydrocarbon group having 1-6 carbon atoms, preferably each independently a hydrogen atom or a saturated or unsaturated straight chain or branched chain hydrocarbon group having 1-6 carbon atoms.

Examples of the "saturated or unsaturated straight chain or branched chain hydrocarbon group having 1-6 carbon atoms" include a methyl group, an ethyl group, an isopropyl group, a propyl group, a butyl group, an isobutyl group, a sec-butyl group, a tert-butyl group, a pentyl group, a sec-pentyl group, a tert-pentyl group, an isopentyl group, a hexyl group and the like. From the aspect of solubility, $R^3$ and $R^4$ are preferably each independently a hydrogen atom or a saturated or unsaturated straight chain or branched chain hydrocarbon group having 1-4 carbon atoms, $R^3$ is more preferably a hydrogen atom, a methyl group or an ethyl group, and $R^4$ is further preferably a hydrogen atom. $R^5$ and $R^6$ are each preferably a hydrogen atom, a methyl group or an ethyl group, more preferably a hydrogen atom.

X, Y and Z are each independently a single bond or an optionally substituted divalent hydrocarbon group, 1-10 carbon atoms in the carbon atoms constituting the hydrocarbon group are optionally substituted by hetero atom(s), and 1-10 carbon atoms in the carbon atoms constituting the hydrocarbon group optionally have oxo group(s).

X and Z are preferably each independently a single bond, or an optionally substituted saturated or unsaturated straight chain or branched chain divalent hydrocarbon group, more preferably each independently a single bond, or an optionally substituted straight chain or branched chain divalent hydrocarbon group having 1-15 carbon atoms. Z is preferably a single bond.

Y is preferably a single bond, or an alicyclic hydrocarbon group (which is optionally substituted by (a) a $C_{1-10}$ alkyl group, (b) a $C_{2-10}$ alkenyl group, and (c) a $C_{2-10}$ alkynyl group), more preferably a single bond, or a 6-membered alicyclic hydrocarbon group (which is optionally substituted by (a) a $C_{1-10}$ alkyl group, (b) a $C_{2-10}$ alkenyl group, and (c) a $C_{2-10}$ alkynyl group), further preferably a single bond.

Here, examples of the divalent hydrocarbon group wherein 1-10 carbon atoms in the carbon atoms constituting the hydrocarbon group are substituted by hetero atom(s) include —O—, —S—, —NH—, —CH$_2$—O—CH$_2$—, —S—(CH$_2$)$_2$—, —(CH$_2$)$_2$—NH—CH$_2$— and the like as substituent wherein one carbon atom in the carbon atoms constituting the alkylene group is substituted by a hetero atom; piperidine-diyl, tetrahydropyran-diyl, piperazine-diyl and the like as substituent wherein 1-2 carbon atoms in the carbon atoms constituting the cycloalkylene group is/are substituted by hetero atom(s); and pyridine-diyl, pyrazine-diyl, pyrimidine-diyl and the like as substituent wherein 1-2 carbon atoms in the carbon atoms constituting arylene is/are substituted by hetero atom(s).

Examples of the divalent hydrocarbon group wherein 1-10 carbon atoms in the carbon atoms constituting the hydrocarbon group have oxo group(s) include —CO—, —CH$_2$—CO—CH$_2$—, —(CH$_2$)$_2$—CO—CH$_2$— and the like as a substituent wherein one carbon atom in the carbon atoms constituting the alkylene group has oxo group(s).

Examples of the divalent hydrocarbon group wherein 1-10 carbon atoms in the carbon atoms constituting the hydrocarbon group are substituted by hetero atom(s), and further, 1-10 carbon atoms in the carbon atoms constituting the hydrocarbon group have oxo group(s), include —CH$_2$—NH—CO—, —CH$_2$—CO—O—, —CH$_2$—NH—CO—NH—CH$_2$— and the like, as substituent wherein 1-2 carbon atoms in the carbon atoms constituting the alkylene group is/are substituted by hetero atom(s), and further one carbon atom has an oxo group.

Preferable examples of the basic amino acid derivative represented by the formula (1) include the following compounds.

(Compound-A)
A compound wherein
an acyl group represented by $R^1$—CO— is an acyl group derived from a straight chain or branched chain saturated fatty acid having 6-18 carbon atoms,
$R^2$ is a hydrogen atom or a saturated or unsaturated straight chain or branched chain hydrocarbon group having 4-10 carbon atoms,
m is an integer of 1-4,
n is an integer of 0-9, and
$R^3$ and $R^4$ are each independently a hydrogen atom or a saturated or unsaturated straight chain or branched chain hydrocarbon group having 1-4 carbon atoms.

(Compound-B)
A compound wherein
an acyl group represented by $R^1$—CO— is a lauroyl group, a myristoyl group, a palmitoyl group or a stearoyl group,
$R^2$ is a hydrogen atom or a saturated or unsaturated straight chain or branched chain hydrocarbon group having 7-10 carbon atoms,
m is 3 or 4,
n is an integer of 0-9,
$R^3$ is a hydrogen atom or a saturated straight chain or branched chain hydrocarbon group having 1-4 carbon atoms, and
$R^4$ is a hydrogen atom.

(Compound-C)
A compound wherein
an acyl group represented by $R^1$—CO— is a lauroyl group,
$R^2$ is a hydrogen atom or a saturated straight chain or branched chain hydrocarbon group having 7-10 carbon atoms,
m is 4,
n is an integer of 0-9,
$R^3$ is a hydrogen atom, a methyl group or an ethyl group, and
$R^4$ is a hydrogen atom.

Examples of the salt of the basic amino acid derivative of the present invention include alkali metal salts such as lithium salt, sodium salt, potassium salt and the like; alkaline earth metal salts such as calcium salt, magnesium salt and the like; ammonium salts such as alkanolamine salt and the like; basic organic salt and the like. Of these, sodium salt, potassium salt or ammonium salt is preferable, sodium salt or potassium salt is more preferable, and sodium salt is further preferable, from the aspect of solubility.

Examples of the basic amino acid derivative of the present invention include the following.

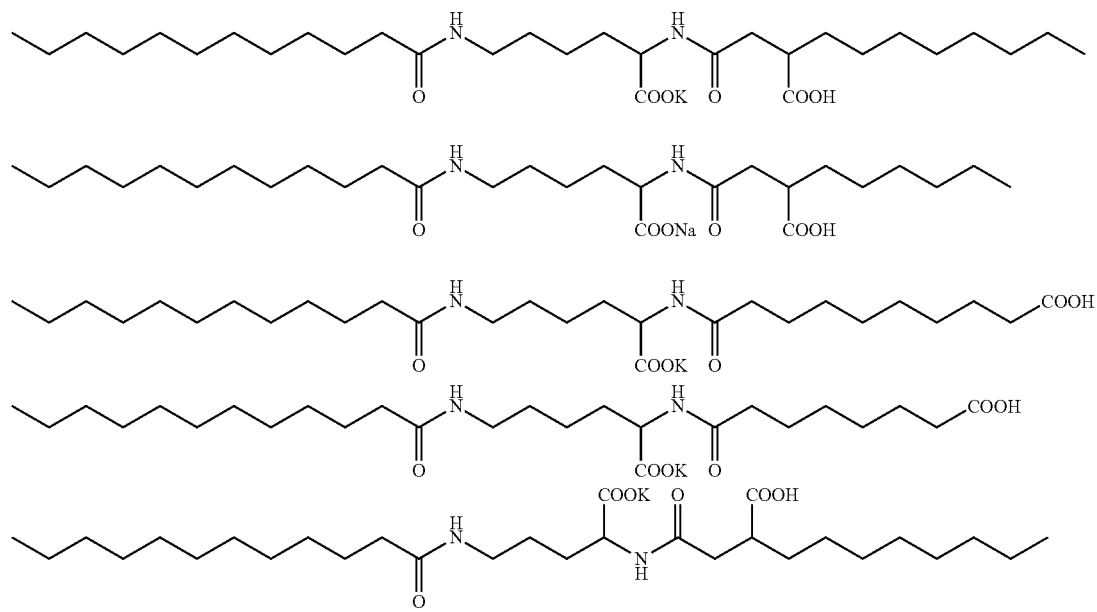

-continued

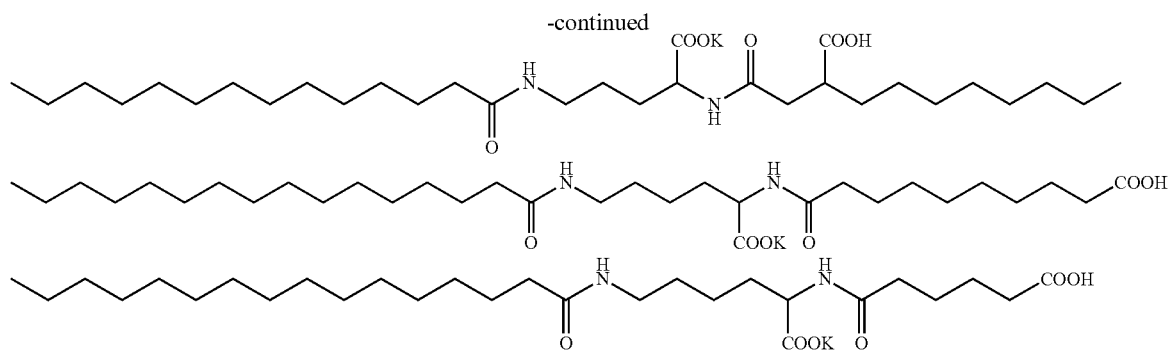

It is preferably one or more kinds selected from the group consisting of $N^\epsilon$-lauroyl-$N^\alpha$-(3-carboxytridecanoyl)-L-lysine ethyl ester, $N^\epsilon$-lauroyl-$N^\alpha$-(3-carboxytridecanoyl)-L-lysine, $N^\epsilon$-lauroyl-$N^\alpha$-(5-carboxypentanoyl)-L-lysine, $N^\epsilon$-lauroyl-$N^\alpha$-(7-carboxyheptanoyl)-L-lysine and $N^\epsilon$-lauroyl-$N^\alpha$-(9-carboxynonanoyl)-L-lysine, and a salt thereof, more preferably $N^\epsilon$-lauroyl-$N^\alpha$-(9-carboxynonanoyl)-L-lysine or a salt thereof.

The basic amino acid derivative of the present invention can be synthesized by a conventional method. For example, using $N^\epsilon$-lauroyl lysine as a starting material, esterification, reaction with an anhydrous succinic acid derivative, and hydrolysis affords the basic amino acid derivative. In addition, the basic amino acid derivative can also be obtained by reacting an ester of $N^\epsilon$-lauroyl lysine with a dicarboxylic acid monochloride monoester, and hydrolyzing the ester. More specific examples are given below.

-continued

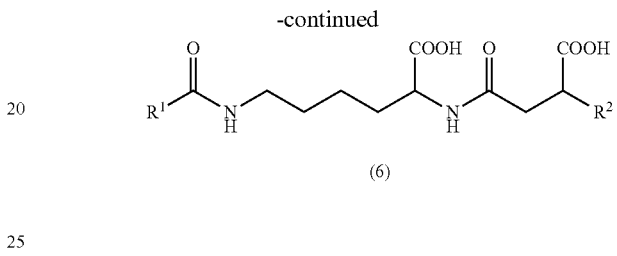

wherein each symbol is as defined in the formula (1).

Compound (3) can be prepared by alkyl esterification of compound (2) in a solvent. Compound (5) can be prepared by reacting compound (3) with an anhydrous dicarboxylic acid derivative such as compound (4) in an appropriate solvent. Thereafter, compound (5) is hydrolyzed by a base such as sodium hydroxide, potassium hydroxide and the like to give compound (6).

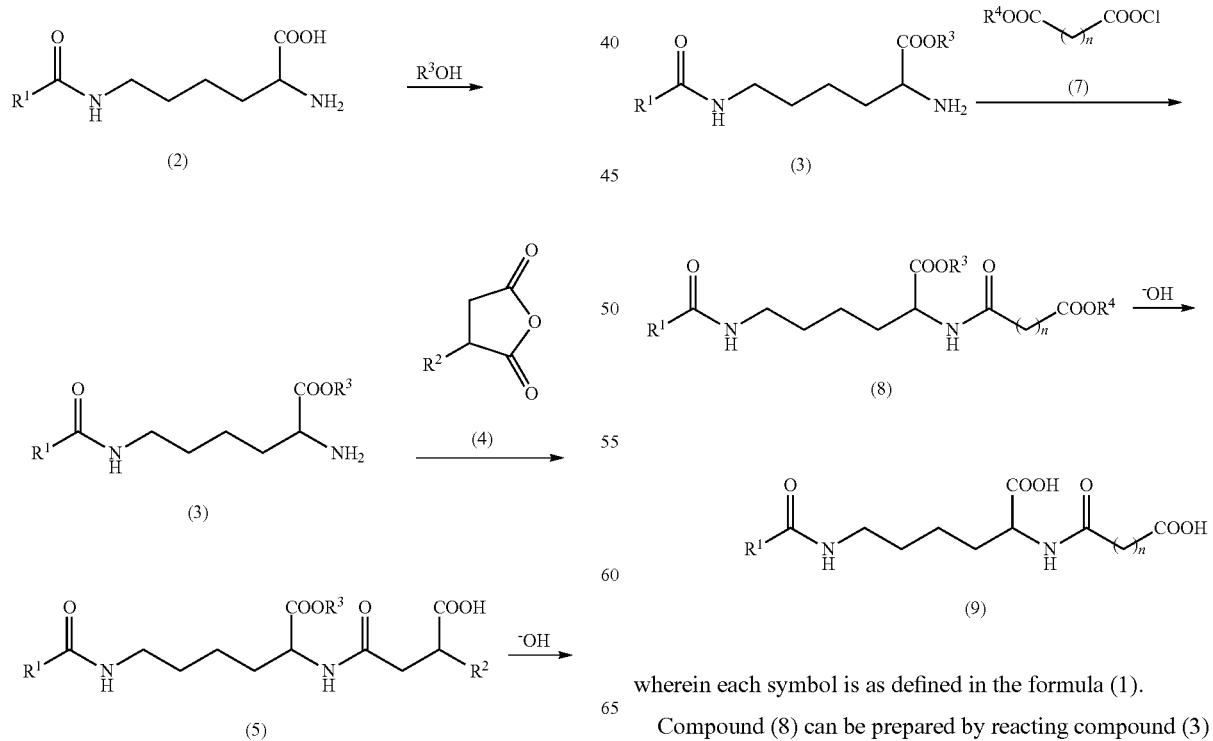

wherein each symbol is as defined in the formula (1).

Compound (8) can be prepared by reacting compound (3) with a dicarboxylic acid monoester monochloride such as compound (7). Compound (9) can be prepared by hydrolyzing compound (8) by a general base such as sodium hydroxide, potassium hydroxide and the like.

The basic amino acid derivative represented by the formula (1A) and the formula (1B) of the present invention can be produced according to the above-mentioned production method and using, instead of compound (7), dicarboxylic acid monoester monochloride represented by $R^4OOC$—X—Y—Z—COOCl or $R^4OOC$—X—COOCl wherein each symbol is as defined in the formula (1A) and the formula (1B). When the dicarboxylic acid monoester monochloride is commercially available, such product can be directly used, or one produced according to a method known per se, or a method analogous thereto, can also be used. Here, dimer acid is also encompassed in the dicarboxylic acid. Dimer acid is a dibasic acid obtained by dimerizing an unsaturated fatty acid.

The present invention also relates to a gelling agent containing the above-mentioned basic amino acid derivative. In the present specification, the gelling agent refers to a substance that thickens a liquid and changes into a jelly or solid form. In the present invention, it is particularly useful as a gelling agent for an aqueous composition. The "aqueous composition" in the present invention means a composition containing water.

Examples of the form of the gelling agent include solid, particle, solution and paste. Excipients and solvents can be used as appropriate. When a solution form is desired, acids such as hydrochloric acid, citric acid, phosphoric acid and the like and bases such as sodium hydroxide and the like can be used to adjust the pH as appropriate. The pH of the gelling agent is preferably 1-14, the upper limit is preferably 13, more preferably 12, and the lower limit is preferably 2, more preferably 3, from the aspect of solubility.

The gelling agent of the present invention is added to an aqueous composition, the mixture is heated to 40-100° C. as necessary, homogeneously stirred, and left standing at room temperature to allow the aqueous composition to be gelled or thickened. The gel hardness or viscosity can be freely adjusted by controlling the amount of the gelling agent of the present invention to be added.

While the amount of the gelling agent to be added to an aqueous composition varies depending on the constitution of the aqueous composition, it is added to 0.0001 wt %-20 wt %, in the weight concentration of the basic amino acid derivative.

The lower limit is more preferably 0.001 wt %, further preferably 0.01 wt %, still more preferably 0.1 wt %, especially preferably 1 wt %. The upper limit is more preferably 15 wt %, further preferably 10 wt %, still more preferably 7 wt %, especially preferably 5 wt %.

The pH for preparation of the gel is preferably 1-14. From the aspect of solubility, the upper limit is preferably 13, more preferably 12, and the lower limit is preferably 2, more preferably 3.

The present invention also relates to a gel composition comprising at least one kind of the above-mentioned basic amino acid derivatives and salts thereof, and water. The gel composition of the present invention is smooth and shows good spinnability. In the present specification, the "spinnability" means the property of stringiness observed after contact with and detachment from a surface coated with the gel composition. The "shows good spinnability" means complete absence of stringiness, or immediately breakage of thread, after contact with and detachment from a surface coated with the gel composition.

The gel composition of the present invention can contain other gelling agents or solidifying agents as long as the effect of the present invention is not impaired. Examples of other gelling agents or solidifying agents include natural polymers such as alginic acid, carageenan, agar, guar gum, curdlan, xanthan gum, pullulan, gellan gum, gelatin, casein, albumin, collagen and the like, semisynthetic polymers such as methylcellulose, ethylcellulose, hydroxyethylcellulose, hydroxypropylcellulose, carboxymethylcellulose, methylhydroxypropylcellulose, soluble starch, carboxymethylstarch, methylstarch, alginic acid propyleneglycol ester and the like, synthetic polymers such as polyvinyl alcohol, polyacrylic acid salt, polyvinylpyrrolidone, polyvinyl methylether, carboxyvinyl polymer, sodium polyacrylate, polyethylene oxide, ethyleneoxide propyleneoxide block copolymer and the like, inorganic substances such as bentonite, laponite, finely divided powder silicon dioxide, colloidal alumina and the like, and the like.

The present invention further relates to a cosmetic agent containing the above-mentioned gel composition. Specific examples of the cosmetic agent of the present invention include adiaphoretic, facial cleanser, cleansing gel, milky lotion, massage cream, cold cream, moisture gel, facial mask, after shaving gel, foundation, chapstick, lipstick, cheek, mascara, shampoo, rinse, hair tonic, treatment, conditioner, tic, set lotion, hair cream, hair wax, hair mousse, perm solution, hair dye, hair coloring, hair manicure, sunscreen oil, hand soap, aromatic and the like.

The cosmetic agent of the present invention can contain various components usable for general cosmetic agent, skin external preparation or quasi-drug as long as the effect of the present invention is not inhibited. Examples thereof include oily component, chelating agent, surfactant, powder, amino acid, amino acid derivative, polyamino acid, lower alcohol, higher alcohol, polyvalent alcohol, sugar alcohol and alkyleneoxide adduct thereof, water-soluble polymer, plant extract, nucleic acid, vitamin, enzyme, gelling agent, humectant, disinfectant and antimicrobial agent, anti-inflammatory agent, analgesic, antifungal agent, stratum corneum softening release agent, skin colorant, hormone agent, ultraviolet ray absorbent, hair tonic, antiperspirant and astringent active ingredient, perspiration deodorant, vitamin, vasodilator, crude drug, pH adjuster, sequestrant, viscosity modifier, pearl ingredient, natural perfume, synthetic perfume, dye, pigment, antioxidant, preservative, emulsifier, fat, wax, silicone compound, balm and the like.

EXAMPLES

The present invention is explained in more detail in the following by referring to Examples, which are not to be construed as limitative.

The instruments used for the measurement of the compounds are the following. IR measurement apparatus: JASCO FS-420 spectrometer, 1H-NMR: Bruker AVANCE400 spectrometer, elemental analysis apparatus: Perkin-Elmer series II CHNS/O analyzer 2400.

Production Example 1

Synthesis of $N^\epsilon$-lauroyl-$N^\alpha$-(3-carboxytridecanoyl)-L-lysine ethyl ester sodium salt (A-Na)

$N^\epsilon$-Lauroyl-L-lysine ethyl ester (29.9 g) was dissolved in dehydrated dichloromethane (650 ml), n-decyl succinic anhydride (21.2 g) was added, and the mixture was stirred at room temperature for 24 hr. The obtained white turbid solution was heated and cooled in a freezer to give crystals. The mixture was filtered, dried, and recrystallized to give $N^\epsilon$-lauroyl-$N^\alpha$-(3-carboxytridecanoyl)-L-lysine ethyl ester (43 g, yield 85%). 4 g thereof was dissolved in distilled ethanol (100 ml), and 4M aqueous NaOH solution (1.68 ml) was added with stirring. The mixture was stirred at room temperature for 3 hr, filtered, dried under reduced pressure, and recrystallized. yield 4.1 g, 97%.

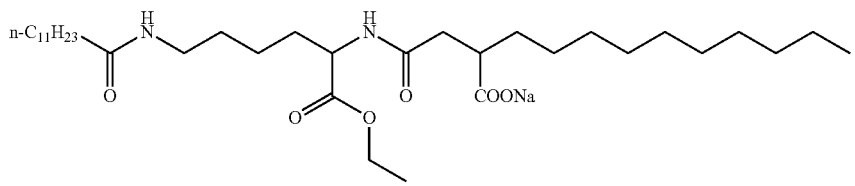

FT-IR(KBr): υ=1735, 1643 cm$^{-1}$. $^1$H-NMR (400 MHz, DMSO-d$_6$, TMS, 25° C.): δ=0.85 (t, J=6.6 Hz, 6H), 2.02 (t, 2H), 2.98 (q, 2H), 2.64 (m, 1H), 3.99-4.09 (m, 2H), 7.69 (t, 1H), 8.23 (d, 1H). Elemental Analysis calcd(%) for C$_{34}$H$_{63}$N$_2$NaO$_6$ (618.86): C, 65.99; H, 10.26; N, 4.53. Found: C, 66.44; H, 10.54; N, 4.62.

Production Example 2

Synthesis of $N^\epsilon$-lauroyl-$N^\alpha$-(3-carboxytridecanoyl)-L-lysine ethyl ester potassium salt (A-K)

Using 4M aqueous KOH solution instead of 4M aqueous NaOH solution, and in the same manner as in Production Example 1, the object product was synthesized. yield 4.2 g, 96%.

FT-IR(KBr): υ=1735, 1643 cm$^{-1}$. $^1$NMR (400 MHz, DMSO-d$_6$, TMS, 25° C.) δ=0.85 (t, J=6.6 Hz, 6H), 2.02 (t, 2H), 2.98 (q, 2H), 2.64 (m, 1H), 3.99-4.09 (m, 2H), 7.69 (t,

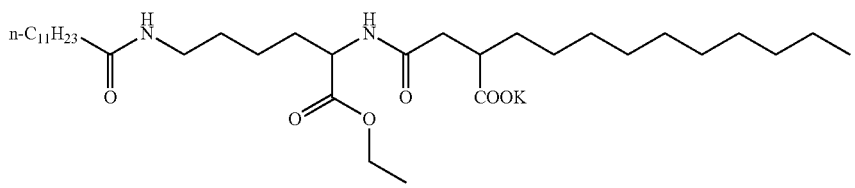

1H), 8.23 (d, 1H). Elemental Analysis calcd(%) for C$_{34}$H$_{63}$KN$_2$O$_6$ (634.97): C, 64.31; H, 10.00; N, 4.41. Found: C, 65.11; H, 10.24; N, 4.52.

Production Example 3

Synthesis of $N^\epsilon$-lauroyl-$N^\alpha$-(3-carboxytridecanoyl)-L-lysine monosodium salt (B—Na)

$N^\epsilon$-Lauroyl-$N^\alpha$-(3-carboxytridecanoyl)-L-lysine ethyl ester (30 g) obtained as in Production Example 1 was dissolved in distilled methanol (500 ml), 1M aqueous NaOH solution (110 ml) was added, and the mixture was stirred for 24 hr. Distilled water (1.5 L) was added to the obtained solution, and concentrated hydrochloric acid (50 ml) was added with vigorous stirring. The obtained crystals were filtered off, and the crystals were recrystallized to give $N^\epsilon$-lauroyl-$N^\alpha$-(3-carboxytridecanoyl)-L-lysine (21 g, yield 73%). 4 g thereof was dissolved in distilled methanol (50 ml), and 1M aqueous NaOH solution (7 ml) was added with stirring. The obtained mixture containing white sediment was stirred at 50° C. for 30 min, hot filtered and recrystallized. yield 3.3 g, 80%.

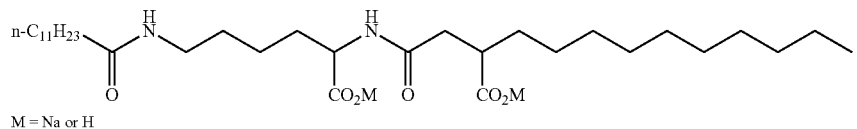

M = Na or H

FT-IR(KBr): υ=1669, 1643 cm$^{-1}$. $^1$H-NMR (400 MHz, DMSO, TMS, 25° C.) δ=0.85 (t, J=6.6 Hz, 6H), 2.02 (t, 2H), 2.98 (q, 2H), 2.64 (m, 1H), 7.69 (t, 1H), 8.23 (d, 1H). Elemental Analysis calcd(%) for $C_{32}H_{59}N_2NaO_6$ (590.81): C, 65.05; H, 10.07; N, 4.74. Found: C, 65.22; H, 10.17; N, 4.79.

Production Example 4

Synthesis of N$^ε$-lauroyl-N$^α$-(3-carboxytridecanoyl)-L-lysine monopotassium salt (B—K)

Using N$^ε$-lauroyl-N$^α$-(3-carboxytridecanoyl)-L-lysine (4.0 g) obtained in Production Example 3 and 1M aqueous KOH solution instead of 1M aqueous NaOH solution, and in the same manner as in Production Example 3, the object product was synthesized. yield 4.2 g, 99%.

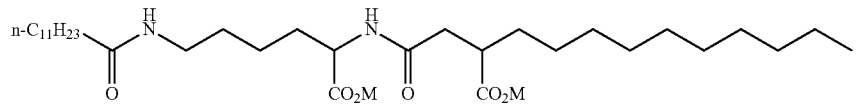

M = K or H

FT-IR(KBr): υ=1700, 1644 cm$^{-1}$. $^1$H-NMR (400 MHz, DMSO-d$_6$, TMS, 25° C.): δ=0.85 (t, J=6.6 Hz, 6H), 2.02 (t, 2H), 2.98 (q, 2H), 2.64 (m, 1H), 7.69 (t, 1H), 8.23 (d, 1H). Elemental Analysis calcd(%) for $C_{32}H_{59}KN_2O_6$ (606.92): C, 63.33; H, 9.80; N, 4.62. Found: C, 64.01; H, 9.99; N, 4.66.

Production Example 5

Synthesis of N$^ε$-lauroyl-N$^α$-(5-carboxypentanoyl)-L-lysine monosodium salt (NaAmiC$_5$CO$_2$H)

N$^ε$-Lauroyl-L-lysine (30 g) was dissolved in 0.2M aqueous NaOH solution (1 L), and ether was added. Adipic acid monoethyl ester acid chloride (26.4 g) was added to the ether layer, and the mixture was stirred at room temperature for 24 hr. To the aqueous solution was added hydrochloric acid with stirring, and the mixture was adjusted to about pH 1. The precipitated crystals were filtered and recrystallized to give N$^ε$-lauroyl-N$^α$-(5-carboxypentanoyl)-L-lysine (27.42 g, yield 66%). 4.566 g thereof was dissolved in methanol (50 ml), 1M aqueous NaOH solution (10 ml) was added, and the mixture was stirred at room temperature for 3 hr. The solution was filtered, the solvent was removed, and the obtained solid was recrystallized. yield 4.7 g, 99%.

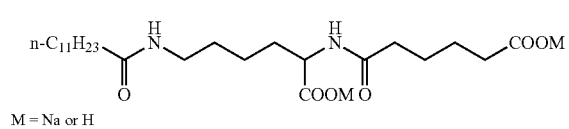

M = Na or H

FT-IR(KBr): υ=3300, 1701, 1638, 1592, 1551 cm$^{-1}$. $^1$H-NMR (400 MHz, CDCl$_3$:DMSO-d$_6$ (5:5), TMS, 25° C.): δ=0.87 (t, J=6.9 Hz, 3H), 1.23 (br, 18H), 1.32-1.36 (m, 2H), 1.39-1.44 (m, 6H), 1.46-1.68 (m, 2H), 2.05 (t, J=7.6 Hz, 2H), 2.14 (t, J=6.6 Hz, 2H), 2.17 (t, J=6.6 Hz, 2H), 2.01 (q, J=6.4 Hz, 2H), 4.04 (q, J=6.5 Hz, 1H), 7.44 (d, J=7.6 Hz, 1H), 7.65 (d, J=5.4 Hz, 1H). Elemental Analysis calcd(%) for $C_{24}H_{43}N_2NaO_6$ (478.60): C, 60.23; H, 9.06; N, 5.85. Found: C, 60.55; H, 9.22; N, 5.88.

Production Example 6

Synthesis of N$^ε$-lauroyl-N$^α$-(5-carboxypentanoyl)-L-lysine monopotassium salt (KAmiC$_5$CO$_2$H)

Using N$^ε$-lauroyl-N$^α$-(5-carboxypentanoyl)-L-lysine (4.566 g) obtained in Production Example 5 and 1M aqueous KOH solution instead of 1M aqueous NaOH solution, and in the same manner as in Production Example 5, the object product was synthesized. yield 4.6 g, 99%.

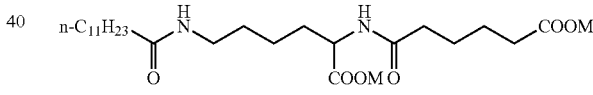

M = K or H

FT-IR(KBr): υ=3302, 1709, 1637, 1586, 1550 cm$^{-1}$. $^1$H-NMR (400 MHz, CDCl$_3$:DMSO-d$_6$ (5:5), TMS, 25° C.): δ=0.85 (t, J=6.8 Hz, 3H), 1.23 (br, 18H), 1.32-1.36 (m, 2H), 1.39-1.44 (m, 6H), 1.46-1.68 (m, 2H), 2.02 (t, J=7.3 Hz, 2H), 2.06-2.11 (m, 2H), 2.13-2.16 (m, 2H), 2.95 (q, J=6.5 Hz, 2H), 3.84 (q, J=6.4 Hz, 1H), 7.39 (d, J=7.3 Hz, 1H), 7.78 (t, J=5.3 Hz, 1H). Elemental Analysis calcd(%) for $C_{24}H_{43}KN_2O_6$ (494.71): C, 58.27; H, 8.76; N, 5.66. Found: C, 59.00; H, 8.88; N, 5.70.

Production Example 7

Synthesis of N$^ε$-lauroyl-N$^α$-(7-carboxyheptanoyl)-L-lysine monosodium salt (NaAmiC$_7$CO$_2$H)

Using suberic acid monomethyl acid chloride (17.1 ml) instead of adipic acid monoethyl ester acid chloride (26.4 g), and in the same manner as in Production Example 5, N$^ε$-lauroyl-N$^α$-(7-carboxyheptanoyl)-L-lysine was synthesized. yield: 30 g, 70%. Using 4.85 g thereof instead of N$^ε$-lauroyl-N$^α$-(5-carboxypentanoyl)-L-lysine, and in the same manner as in Production Example 5, the object product was synthesized. yield 5.0 g, 99%.

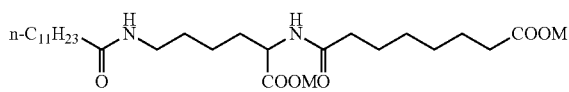

M = Na or H

FT-IR(KBr): υ=3302, 1707, 1639, 1592, 1551 cm$^{-1}$.
$^1$H-NMR (400 MHz, CDCl$_3$:DMSO-d$_6$ (5:5), TMS, 25° C.): δ=0.85 (t, J=6.8 Hz, 3H), 1.23 (br, 22H), 1.30-1.35 (m, 2H), 1.36-1.42 (m, 6H), 1.43-1.66 (m, 2H), 2.02 (t, J=7.5 Hz, 2H), 2.08 (t, J=7.3 Hz, 2H), 2.13 (t, J=7.3 Hz, 2H), 2.97 (q, J=6.5 Hz, 2H), 3.95 (q, J=6.5 Hz, 1H), 7.44 (d, J=7.6 Hz, 1H), 7.75 (t, J=5.4 Hz, 1H). Elemental Analysis calcd(%) for C$_{26}$H$_{47}$N$_2$NaO$_6$ (506.65): C, 61.64; H, 9.35; N, 5.53. Found: C, 61.88; H, 9.57; N, 5.63.

Production Example 8

Synthesis of N$^ε$-lauroyl-N$^α$-(7-carboxyheptanoyl)-L-lysine monopotassium salt (KAmiC$_7$CO$_2$H)

Using N$^ε$-lauroyl-N$^α$-(7-carboxyheptanoyl)-L-lysine (4.85 g) obtained in Production Example 7 instead of N$^ε$-lauroyl-N$^α$-(5-carboxypentanoyl)-L-lysine and 1M aqueous KOH solution instead of 1M aqueous NaOH solution, and in the same manner as in Production Example 5, the object product was synthesized. yield 5.15 g, yield 99%.

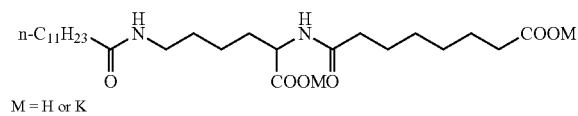

M = H or K

FT-IR(KBr): υ=3303, 1708, 1639, 1585, 1550 cm$^{-1}$.
$^1$H-NMR (400 MHz, CDCl$_3$:DMSO-d$_6$ (5:5), TMS, 25° C.): δ=0.85 (t, J=6.8 Hz, 3H), 1.23 (br, 22H), 1.30-1.35 (m, 2H), 1.36-1.42 (m, 6H), 1.43-1.66 (m, 2H), 2.01 (t, J=7.5 Hz, 2H), 2.04-2.08 (m, 2H), 2.10-2.14 (m, 2H), 2.95 (q, J=6.3 Hz, 2H), 3.83 (q, J=6.4 Hz, 1H), 7.31 (d, J=7.1 Hz, 1H), 7.76 (t, J=5.3 Hz, 1H). Elemental Analysis calcd(%) for C$_{26}$H$_{47}$KN$_2$O$_6$ (522.76): C, 59.74; H, 9.06; N, 5.36. Found: C, 60.01; H, 9.22; N, 5.39.

Production Example 9

Synthesis of N$^ε$-lauroyl-N$^α$-(9-carboxynonanoyl)-L-lysine monosodium salt (NaAmiC$_9$CO$_2$H)

Using sebacic acid monomethyl acid chloride (30.5 g, 0.13 mol) instead of adipic acid monoethyl ester acid chloride (26.4 g), and in the same manner as in Production Example 5, N$^ε$-lauroyl-N$^α$-(9-carboxynonanoyl)-L-lysine was synthesized. yield: 35 g, yield 75%. Using 5.13 g thereof instead of N$^ε$-lauroyl-N$^α$-(5-carboxypentanoyl)-L-lysine, and in the same manner as in Production Example 5, the object product was synthesized. yield 5.3 g, 99%.

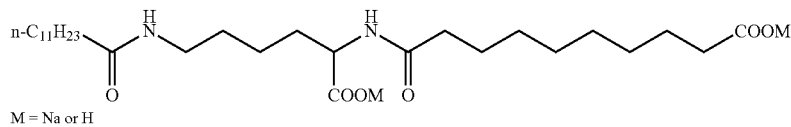

M = Na or H

FT-IR(KBr): υ=3304, 1703, 1641, 1594, 1550 cm$^{-1}$.
$^1$H-NMR (400 MHz, CDCl$_3$:DMSO-d$_6$ (5:5), TMS, 25° C.): δ=0.85 (t, J=6.7 Hz, 3H), 1.23 (br, 26H), 1.30-1.35 (m, 2H), 1.36-1.42 (m, 6H), 1.43-1.66 (m, 2H), 2.02 (t, J=7.6 Hz, 2H), 2.08 (t, J=7.3 Hz, 2H), 2.12 (t, J=7.5 Hz, 2H), 2.96 (q, J=6.5 Hz, 2H), 3.92 (q, J=6.5 Hz, 1H), 7.37 (d, J=7.3 Hz, 1H), 7.74 (t, J=5.4 Hz, 1H). Elemental Analysis calcd(%) for C$_{28}$H$_{51}$N$_2$NaO$_6$ (534.70): C, 62.89; H, 9.61; N, 5.24. Found: C, 63.00; H, 9.77; N, 5.29.

Production Example 10

Synthesis of N$^ε$-lauroyl-N$^α$-(9-carboxynonanoyl)-L-lysine monopotassium salt (KAmiC$_9$CO$_2$H)

Using N$^ε$-lauroyl-N$^α$-(9-carboxynonanoyl)-L-lysine (5.13 g) obtained in Production Example 9 instead of N$^ε$-lauroyl-N$^α$-(5-carboxypentanoyl)-L-lysine and 1M aqueous KOH solution instead of 1M aqueous NaOH solution, and in the same manner as in Production Example 5, the object product was synthesized. yield 5.4 g, 99%.

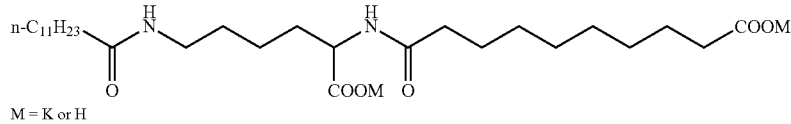

M = K or H

FT-IR(KBr): υ=3304, 1703, 1640, 1585, 1550 cm$^{-1}$.
$^1$H-NMR (400 MHz, CDCl$_3$:DMSO-d$_6$ (5:5), TMS, 25° C.): δ=0.85 (t, J=6.7 Hz, 3H), 1.23 (br, 26H), 1.30-1.35 (m, 2H), 1.36-1.42 (m, 6H), 1.43-1.66 (m, 2H), 2.01 (t, J=7.5 Hz, 2H), 2.07 (t, J=7.3 Hz, 2H), 2.10-2.14 (m, 2H), 2.95 (q, J=6.5 Hz,

2H), 3.85 (q, J=6.4 Hz, 1H), 7.34 (d, J=7.3 Hz, 1H), 7.76 (t, J=5.4 Hz, 1H). Elemental Analysis calcd(%) for $C_{28}H_{51}KN_2O_6$ (550.81): C, 61.06; H, 9.33; N, 5.09. Found: C, 61.55; H, 9.57; N, 5.22.

<Gelling Ability of Various Derivatives>

The gelling ability of various basic amino acid derivatives prepared in Production Examples 1-4, 7, 9 and 10 was confirmed. Test tube equipped with a cover was filled with water, saline, phosphate buffered saline (hereinafter indicated as PBS), and aqueous NaCl solution or aqueous KCl solution, and a basic amino acid derivative was added at various concentrations. The mixture was heated to 100° C. to achieve homogeneous dissolution, and stood at 25° C. for 2 hr. After allowing to cool, the test tube was tilted, and the absence of fluidity was judged as gellation, and the appearance was visually observed. The results are shown below.

Abbreviations mean the following.
GT: transparent gel
GTL: translucent gel
GO: opaque gel The number in the parenthesis shows minimum gelling concentration (g/L).

Compound of Production Example 1 water: GTL (25), saline: GTL (20), 0.1M aqueous NaCl solution: GTL (10), 0.1M aqueous KCl solution: GTL (15)

Compound of Production Example 2 water: GTL (20), saline: GTL (20), 0.1M aqueous NaCl solution: GTL (10), 0.1M aqueous KCl solution: GTL (10)

Compound of Production Example 3 water: GTL (50), saline: GTL (50), PBS: GO (60), 0.1M aqueous NaCl solution: GTL (20), 0.1M aqueous KCl solution: GTL (20), 1.0M aqueous KCl solution: GO (20)

Compound of Production Example 4 water: GTL (60), saline: GTL (50), PBS: GO (60), 0.1M aqueous NaCl solution: GTL (20), 0.1M aqueous KCl solution: GTL (40), 1.0M aqueous KCl solution: GO (20)

Compound of Production Example 7 saline: GT (30), PBS: GT (30), 0.1M aqueous NaCl solution: GTL (30), 1.0M aqueous NaCl solution: GT (4), 0.1M aqueous KCl solution: GT (30), 1.0M aqueous KCl solution: GT (4)

Compound of Production Example 9 water: GTL (30), saline: GT (4), PBS: GT (4), 0.1M aqueous NaCl solution: GT (4), 1.0M aqueous NaCl solution: GT (4), 0.1M aqueous KCl solution: GT (4), 1.0M aqueous KCl solution: GT (4)

Compound of Production Example 10 water: GTL (30), saline: GT (4), PBS: GT (4), 0.1M aqueous NaCl solution: GT (10), 1.0M aqueous NaCl solution: GT (4), 0.1M aqueous KCl solution: GT (4), 1.0M aqueous KCl solution: GT (4)

It is clear that the basic amino acid derivative of the present invention can gel various aqueous compositions by the addition of a small amount thereof.

Formulation Example 1

Preparation of Skin Lotion Gel

Components A shown below were dissolved by mixing at 70° C., and component B was gradually added at 70° C. Components C mixed by heating to 70° C. were further added, and the mixture was cooled to give a gelled skin lotion. The prepared gel was smooth, free of spinnability and superior in feeling, even though it was a solid. Moreover, the prepared gel showed no syneresis even after 1 week at room temperature and was stable.

TABLE 1

|   |   | (mass %) |
|---|---|---|
| A | di(phytosteryl/octyldodecyl)lauroylglutamate *1 | 0.35 |
|   | cetyl octanoate | 0.15 |
|   | PPG-8-ceteth-20 *2 | 0.50 |
|   | PPG-6-decyltetradeceth-30 *3 | 0.50 |
|   | glycerol | 1.25 |
| B | water | 5.00 |
| C | DPG | 2.00 |
|   | BG | 3.00 |
|   | compound of Production Example 10 | 0.20 |
|   | citric acid | q.s. |
|   | water | balance |
|   |   | 100.00 |

*1 "Eldew PS-203" (manufactured by Ajinomoto Co., Inc.)
*2 "Nikkol PBC-44" (manufactured by Nikko Chemicals)
*3 "Nikkol PEN-4630" (manufactured by Nikko Chemicals)

Formulation Example 2

Preparation of Cream

Components A, components B and components C shown below were each dissolved at 85° C., and components A were added to components B with stirring at 85° C. Components C were further added, and the mixture was cooled to give a cream.

TABLE 2

| A | polyglyceryl-10 myristate *1 | 2.20 |
|---|---|---|
|   | polyglyceryl-6 stearate *2 | 1.10 |
|   | preservative | as required |
|   | squalane | 6.00 |
|   | shea butter | 2.00 |
|   | macadamia nut oil | 4.00 |
|   | di(phytosteryl/octyldodecyl)lauroylglutamate *3 | 0.50 |
| B | stearic acid | 4.00 |
|   | cetanol | 3.50 |
|   | octyldodecanol | 3.20 |
|   | BG | 5.00 |
|   | dibutyllauroyl glutamide *4 | 0.48 |
|   | dibutylethylhexanoyl glutamide *5 | 0.32 |
| C | arginine | 0.05 |
|   | compound of Production Example 9 | 0.30 |
|   | preservative | as required |
|   | water | balance |
|   |   | 100.00 |

*1 "Nikkol Decaglyn 1-M" (manufactured by Nikko Chemicals)
*2 "Nikkol Hexaglyn 1-S" (manufactured by Nikko Chemicals)
*3 "Eldew PS-203" (manufactured by Ajinomoto Co., Inc.)
*4 "GP-1" (manufactured by Ajinomoto Co., Inc.)
*5 "EB-21" (manufactured by Ajinomoto Co., Inc.)

Formulation Example 3

Preparation of Milky Lotion

Components C shown below were dispersed, and added to components B to give an aqueous phase. The aqueous phase was heated to 80° C., components A heated in the same manner were added, and the mixture was emulsified. Components D were further added, and the mixture was emulsified and cooled with stirring to room temperature to give a milky lotion.

TABLE 3

| A | triethylhexanoin | 3.00 |
| --- | --- | --- |
|  | dimethicone | 1.50 |
|  | glyceryl stearate | 0.50 |
|  | polyglyceryl distearate *1 | 1.50 |
|  | myristoylmethyl-β-alanine(phytosteryl/decyltetradecyl) *2 | 3.00 |
| B | glycerol | 20.00 |
|  | BG | 10.00 |
|  | hydrogenated lecithin | 0.50 |
|  | preservative | q.s. |
|  | water | balance |
| C | (acrylic acid/alkyl acrylate(C10-30)) copolymer *3 | 0.10 |
|  | water | 9.90 |
| D | arginine | 0.10 |
|  | compound of Production Example 9 | 0.20 |
|  | water | 5.00 |
|  |  | 100.00 |

*1 "Emalex OTG" (manufactured by Nihon Emulsion Co., Ltd.)
*2 "Eldew APS-307" (manufactured by Ajinomoto Co., Inc.)
*3 "Carbopol ETD-2020" (manufactured by Lubrizol)

Formulation Example 4

Preparation of Hair Treatment

Component B shown below was sufficiently dispersed in component A, components C were added to component A, and the mixture was dissolved by stirring with heating. Separately-heated components D were gradually added to emulsify the mixture. After cooling, components E were added to prepare a m hair treatment.

TABLE 4

| A | purified water | balance |
| --- | --- | --- |
| B | hydroxyethylcellulose | 0.02 |
| C | lactic acid | 0.01 |
|  | methylparaben | 0.2 |
|  | EDTA-2Na | 0.05 |
| D | steartrimonium chloride | 2.00 |
|  | cetanol | 4.00 |
|  | hexyldecyl isostearate | 2.00 |
| E | PCA-Na *1 | 4.00 |
|  | water | 10.00 |
|  | compound of Production Example 10 | 0.20 |
|  | dimethicone | 2.00 |
|  | flavor | q.s. |
|  |  | 100.00 |

*1 "Ajidew NL-50" (manufactured by Ajinomoto Co., Inc.)

Formulation Example 5

Preparation of Sunscreen

Components A shown below were dissolved by heating, and components C were added. Components B were further added, and the mixture was sufficiently dispersed to give an oil phase. Components D were separately dissolved by heating. After cooling, the mixture was added to the oil phase at room temperature to emulsify the mixture, whereby a sunscreen was prepared.

TABLE 5

| A | isopropyl lauroylsarcosinate *1 | 5.80 |
| --- | --- | --- |
|  | glyceryl tri(capryl/capric acid) | 15.00 |
|  | dimethicone *2 | 2.00 |
|  | isononyl isononanoate | 2.00 |
|  | triisostearic acid PEG-10 hydrogenated castor oil *3 | 3.00 |
|  | PEG-11 methyletherdimethicone *4 | 1.50 |
|  | triisostearic acid PEG-20 hydrogenated castor oil *5 | 0.50 |
|  | oxybenzone-3 *6 | 5.00 |
| B | zinc oxide *7 | 5.00 |
|  | titanium oxide *8 | 5.00 |
|  | lauroyllysine *9 | 1.00 |
| C | quarternium-18 bentonite *10 | 1.00 |
|  | glyceryl tri(capryl/capric acid) | 9.00 |
|  | isopropyl lauroylsarcosinate | 0.20 |
| D | NaCl | 0.50 |
|  | phenoxyethanol | 0.30 |
|  | compound of Production Example 3 | 0.05 |
|  | water | balance |
|  |  | 100.00 |

*1 "Eldew SL-205" (manufactured by Ajinomoto Co., Inc.)
*2 "TSF451-5A" (manufactured by Momentive Performance Materials Inc.)
*3 "Emalex RWIS-310" (manufactured by Nihon Emulsion Co., Ltd.)
*4 "KF-351A" (manufactured by Shin-Etsu silicone)
*5 "Emalex RWIS-320" (manufactured by Nihon Emulsion Co., Ltd.)
*6 "Escalol 567" (manufactured by ISP)
*7 "MZ-303S" (manufactured by Tayca)
*8 "MT-100Z" (manufactured by Tayca)
*9 "Amihope LL" (manufactured by Ajinomoto Co., Inc.)
*10 "S-BEN(W)" (manufactured by HOJUN Co., Ltd.)

Formulation Example 6

Preparation of Facial Cleanser

Components A shown below were dissolved by heating, components B, C and D were added in this order, and the mixture was cooled. Component E was further added to prepare a facial cleanser.

TABLE 6

| A | cocoylglutamic acid K(30%) *1 | 15.0 |
| --- | --- | --- |
|  | cocoylalanine Na(30%) *2 | 25.0 |
|  | lauroylmethylalanine Na(30%) *3 | 10.0 |
|  | myristic acid K | 1.0 |
|  | lauryl glycol hydroxypropylether *4 | 2.0 |
|  | BG | 3.0 |
|  | glycerol | 2.0 |
|  | glyceryl laurate | 2.0 |
|  | water | balance |
|  | compound of Production Example 9 | 0.5 |
|  | glycol distearate *5 | 1.0 |
|  | preservative | q.s. |
| B | hydroxypropylmethylcellulose *6 | 1.0 |
| C | magnesium chloride | 0.5 |
| D | citric acid (20% aqueous solution) | 5.6 |
| E | flavor | q.s. |
|  |  | 100.00 |

*1 "Amisoft CK-22" (manufactured by Ajinomoto Co., Inc.)
*2 "Amilite ACS-12" (manufactured by Ajinomoto Co., Inc.)
*3 "Alanone ALE" (manufactured by Kawaken Fine Chemicals)
*4 "Viscosafe LPE" (manufactured by Kawaken Fine Chemicals)
*5 "Emalex EG-di-SE" (manufactured by Nihon Emulsion Co., Ltd.)
*6 "Metolose 60SH-4000" (manufactured by Shin-Etsu Chemical Co., Ltd.)

INDUSTRIAL APPLICABILITY

According to the compound of the present invention, various aqueous compositions containing salt, acid and the like can be gelled, and a stable gelled compound can be provided. In addition, the compound is considered to be also effective as emulsifier, surfactant, feeling improvement agent, oil gelling agent.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (1):

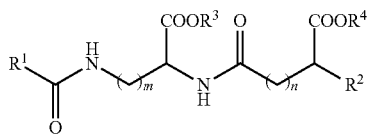

(1)

wherein $R^1$—CO— is a lauroyl group;

$R^2$ is a hydrogen atom or a saturated or unsaturated, straight chain or branched chain hydrocarbon group having 1 to 15 carbon atoms;

m is 4;

n is an integer of 0 to 9; and $R^3$ and $R^4$ are each independently a hydrogen atom, or a saturated or unsaturated, straight chain or branched chain hydrocarbon group having 1 to 6 carbon atoms, or a salt thereof.

2. The compound according to claim 1, which is selected from the group consisting of:

$N^\epsilon$-lauroyl-$N^\alpha$-(3-carboxytridecanoyl)-L-lysine ethyl ester, $N^\epsilon$-lauroyl-$N^\alpha$-(3-carboxytridecanoyl)-L-lysine, $N^\epsilon$-lauroyl-$N^\alpha$-(5-carboxypentanoyl)-L-lysine, $N^\epsilon$-lauroyl-$N^\alpha$-(7-carboxyheptanoyl)-L-lysine, and $N^\epsilon$-lauroyl-$N^\alpha$-(9-carboxynonanoyl)-L-lysine, or a salt thereof.

3. The compound according to claim 1, which is $N^\epsilon$-lauroyl-$N^\alpha$-(9-carboxynonanoyl)-L-lysine or a salt thereof.

4. A gelling agent, comprising at least one compound according to claim 1 or a salt thereof.

5. A gel composition, comprising at least one compound according to claim 1 or a salt thereof, and water.

6. A cosmetic agent, comprising a gel composition according to claim 5.

* * * * *